(12) United States Patent
Toshida

(10) Patent No.: US 8,604,781 B2
(45) Date of Patent: Dec. 10, 2013

(54) CRACK DETERMINING DEVICE AND SEMICONDUCTOR DEVICE

(75) Inventor: Hisamitsu Toshida, Toyota (JP)

(73) Assignee: Toyota Jidosha Kabushiki Kaisha, Toyota-shi, Aichi-ken (JP)

( * ) Notice: Subject to any disclaimer, the term of this patent is extended or adjusted under 35 U.S.C. 154(b) by 0 days.

(21) Appl. No.: 13/376,204

(22) PCT Filed: Jun. 9, 2010

(86) PCT No.: PCT/JP2010/059734
§ 371 (c)(1),
(2), (4) Date: Dec. 5, 2011

(87) PCT Pub. No.: WO2011/155032
PCT Pub. Date: Dec. 15, 2011

(65) Prior Publication Data
US 2013/0076347 A1    Mar. 28, 2013

(51) Int. Cl.
*G01N 27/82*    (2006.01)
(52) U.S. Cl.
USPC ............ 324/219; 324/235; 324/328; 324/240
(58) Field of Classification Search
USPC .................................. 324/219, 235, 238, 240
See application file for complete search history.

(56) References Cited

FOREIGN PATENT DOCUMENTS

| JP | 9-148523 | 6/1997 |
|---|---|---|
| JP | 2005-259753 | 9/2005 |
| JP | 2007-40817 | 2/2007 |
| JP | 2008-140800 | 6/2008 |
| JP | 2009-232261 | 10/2009 |
| JP | 2009-264959 | 11/2009 |

*Primary Examiner* — Reena Aurora
(74) *Attorney, Agent, or Firm* — Finnegan, Henderson, Farabow, Garrett & Dunner, LLP (57) ABSTRACT

There are provided a crack determining device capable of determining, in real time and with precision, the fact that a crack has occurred in a solder layer, and a semiconductor device comprising same. A crack determining device of the present invention is a crack determining device that determines whether or not a crack has occurred in a solder layer with respect to a semiconductor device in which at least a semiconductor element is connected to a connectee member via the solder layer, the crack determining device comprising a generation part that generates a magnetic field and that is fixed to a member forming the semiconductor device, and a detection part that detects a magnitude of a magnetic field and that is disposed within the solder layer, wherein the magnetic field generated at the generation part is detected at the detection part, and it is determined that a crack has occurred in the solder layer if this magnitude of the magnetic field varies from a magnitude of the magnetic field detected before the crack occurred.

13 Claims, 8 Drawing Sheets

CRACK DETERMINING DEVICE AND SEMICONDUCTOR DEVICE

CROSS-REFERENCE TO RELATED APPLICATIONS

This application is a national phase application of International Application No. PCT/JP2010/059734, filed Jun. 9, 2010, the contents of which are incorporated herein by reference.

TECHNICAL FIELD

The present invention relates to a crack determining device that detects the presence/absence of a crack that may occur in a solder layer that connects an element of a semiconductor device with a connectee member, such as a substrate, etc., and to a semiconductor device comprising this crack determining device.

BACKGROUND ART

With respect to semiconductor devices (power modules) in which a semiconductor element such as an IGBT (Insulated Gate Bipolar Transistor), etc., is mounted, adjustments are made whereby the heat generated at this semiconductor element is efficiently dissipated so as to keep it at or below a reference temperature even while heat is generated.

Figure 13:
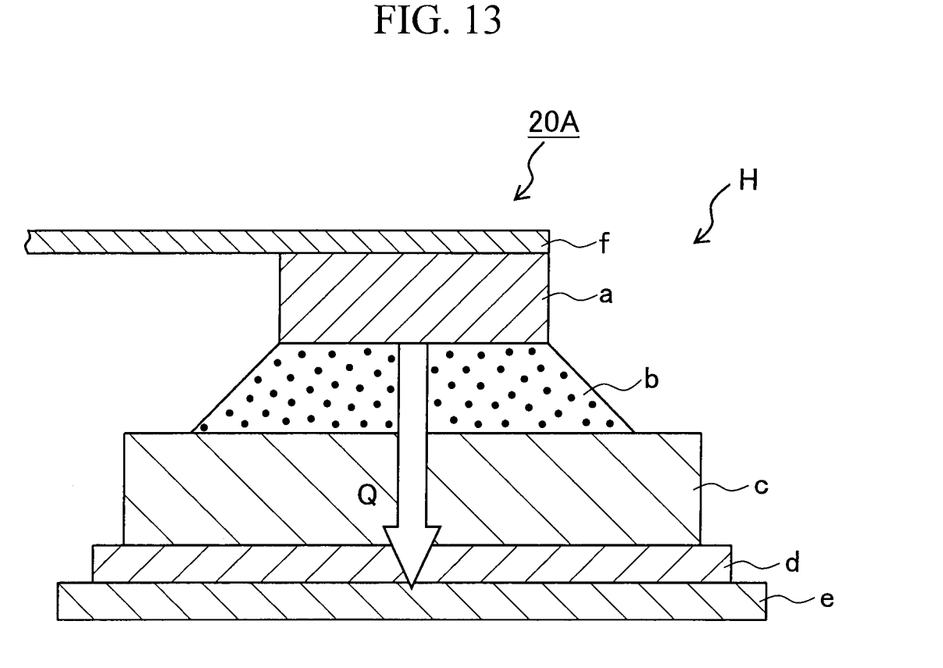
FIG. 13 is a schematic view illustrating the structure of a conventional semiconductor device.

A conventional semiconductor device packaging structure will now be described based on FIG. 13. As shown in the diagram, a circuit board c is fixed on one side of an insulating substrate d comprising an aluminum nitride (AlN) substrate, or a pure aluminum substrate, etc. A semiconductor element a, which is electrically connected with a lead frame f that communicates with an external electrode, and the circuit board c are fixed by means of a solder layer b. A heat sink e for dissipating the heat from the semiconductor element a via the circuit board c (Q direction) is disposed on the other side of the insulating substrate d. A semiconductor device H is thus configured. It is noted that there are a wide variety of configurations for the semiconductor device in addition to that of the illustrated example, examples of which may include a configuration in which a cooler and the like are brazed below the heat sink, a configuration in which the illustrated device is potted with an encapsulating resin body, a configuration in which the semiconductor element is brazed onto the heat sink or the lead frame, etc.

In all of the configurations above, the fact remains that a semiconductor element is connected via a solder layer of a substrate, etc., and that the semiconductor device is of a multi-layered laminate structure of various constituent members. For example, in the illustrated example, the linear expansion rate (or the linear expansion coefficient) of the semiconductor element is approximately 3 ppm/K, the linear expansion rates of the circuit board and the insulating substrate are approximately 4 to 5 ppm/K, the linear expansion rate of the aluminum heat sink is approximately 25 ppm/K. Thus, the linear expansion rates vary significantly from constituent member to constituent member.

If the above-mentioned semiconductor device is to be mounted on hybrid vehicles or electric vehicles, it would have to be made sure that the semiconductor device would withstand, over extended periods, extreme temperature cycles. However, since the linear expansion rates vary significantly from constituent member to constituent member as mentioned above, if the members were to be joined with one another directly, thermal stress would be caused within the constituent members or at the joint interfaces among the constituent members due to differences in linear expansion caused by the change in temperature. Thus, the interior of the solder layer, which is weakest structurally and in strength among the constituent members, would be particularly prone to cracks, and this may become a significant factor in causing the durability of the semiconductor device to drop.

In particular, modem semiconductor devices have seen their miniaturization advance, and the heat generated by semiconductor elements has further increased with this miniaturization of semiconductor devices. Thus, in view of the fact that the amount of heat per unit area has increased, occurrences of cracks in the solder layer mentioned above have become even more pronounced.

Turning now to published prior art, Patent Document 1 discloses a method of detecting the occurrence of a crack based on a temperature difference by detecting the temperatures of respective sites by means of temperature detecting elements disposed at a center part of a semiconductor element and a peripheral end part thereof.

This detection method focuses on the fact that a site where a crack has occurred increases in thermal resistance, thereby impeding heat dissipation, and that the temperature rises as a result thereof. It is thus a method that determines that a crack has occurred at a given site when this site rises in temperature relative to other sites.

However, methods that determine the presence/absence of crack occurrences by measuring the temperature of a given site have the following problems.

Specifically, since heat diffuses readily, it may sometimes be determined that there is no temperature difference between a site where a crack has occurred and a site where no crack has occurred. Thus, so-called false detections occur readily, where a crack has actually occurred even though the measured temperature is low, or where there may actually be no crack even though the measured temperature is high.

Further, since it takes time for heat to be conducted, it is difficult to determine cracks in real time.

PRIOR ART DOCUMENTS

Patent Documents

Patent Document 1: JP Patent Application Publication No. 2005-259753 A

SUMMARY OF THE INVENTION

Problems to be Solved by the Invention

The present invention has been made in view of the problems mentioned above, and an object thereof is to provide a crack determining device that is capable of determining, in real time and with precision, that a crack has occurred in a solder layer that connects an element of a semiconductor device with a connectee member, such as a substrate, etc., as well as a semiconductor device comprising this crack determining device.

Means for Solving the Problems

With a view to achieving the object above, a crack determining device according to the present invention is a crack determining device that determines whether or not a crack has occurred in a solder layer with respect to a semiconductor device in which at least a semiconductor element is connected to a connectee member via the solder layer, the crack determining device comprising: a generation part that generates a magnetic field and that is fixed to a member forming the semiconductor device; and a detection part that detects a magnitude of a magnetic field and that is disposed within the solder layer, wherein the magnetic field generated at the generation part is detected at the detection part, and it is determined that a crack has occurred in the solder layer if this magnitude of the magnetic field varies from a magnitude of the magnetic field detected before the crack occurred.

A semiconductor device into which a crack determining device of the present invention is incorporated may be one in which a semiconductor element, a substrate, etc., which are constituent members thereof, are housed within a case, or it may be one of a caseless structure, or further, it may be one in which these constituent members are potted with an encapsulating resin body, as well as one in which they are not. Further, it naturally covers one that comprises a lead frame that communicates with an external electrode. In addition, the term "substrate" as used herein collectively refers to all of a circuit board, an insulating substrate, a heat sink, or a combination of a circuit board and an insulating substrate, or a combination of the above and a heat sink, and so forth.

A crack determining device of the present invention comprises a generation part that generates a magnetic field, and a detection part that is disposed within a solder layer and that detects the magnitude of a magnetic field. It is noted that the term "magnitude of a magnetic field" as used herein may also be referred to as the strength of a magnetic field, and, by way of example, a measured value of magnetic flux density may be taken to be the magnitude of a magnetic field.

Examples of this generation part may include magnets, such as rare-earth magnets, ferrite magnets, alnico magnets, etc., as well as, if the semiconductor device is one that comprises a lead frame that extends to the outside, a coil attached to this lead frame, and so forth.

Further, this generation part may also be a ferromagnetic material, etc., comprising nickel, iron, cobalt, an alloy thereof, etc., that is dispersed within a solder material (tin, tin-silver, tin-copper, tin-silver-copper, tin-zinc-aluminum, etc.) forming the solder layer.

In addition, in cases where a bulk body (e.g., a sphere) comprising such ferromagnetic materials is buried as a thickness maintaining means for the solder layer, this bulk body would also be capable of serving as the generation part mentioned above.

In addition, examples of the detection part that detects the magnitude of a magnetic field may include, by way of example, Hall elements, magnetoresistive elements (MR elements), etc. However, as ones capable of detecting smaller changes in magnitude of a magnetic field, magneto-impedance elements (MI elements) are preferable. It is noted that if the magnitude of the magnetic field to be detected, or the change therein, is small, an amplifier should be incorporated into the detection part.

As discussed above, there are a wide variety of configurations and combinations for the generation part that generates a magnetic field and the detection part that detects the magnitude of the magnetic field generated at this generation part. However, all of these configurations are such that it is determined that a crack has occurred in a solder layer when, with respect to the magnitude of a magnetic field detected in a state where no crack has occurred in the solder layer, a detected value thereof varies.

Once a crack occurs in the solder layer, this solder layer may become crushed in such a manner as to spread laterally, or the lower face of the solder layer may deform in an corrugated manner, and the position of the detection part disposed within this solder layer may thus become displaced from where it was before the crack occurred.

Further, a crack determining device of the present invention utilizes the fact that, as a result of this position displacement of the detection part, the distance between the generation part and the detection part changes, and that, as a result of this change in distance, the magnitude of the magnetic field detected at the detection part changes.

For example, if a crack occurs in the solder layer and the distance between the detection part and the generation part changes and becomes longer, the magnitude of the magnetic field detected at the detection part would become smaller due to the increase in space resistance between the two.

In addition, although there may be cases where, depending on the manner in which a crack occurs, the distance between the detection part and the generation part would become shorter relative to what it was before the crack occurred, the magnitude of the magnetic field detected at the detection part in such cases would conversely become greater. Thus, in either case, the detected magnitude of the magnetic field would vary between before and after the occurrence of the crack.

In other words, unlike the published prior art discussed above, a crack determining device of the present invention does not determine a crack based on a change in temperature at an arbitrary site in the solder layer. Instead, it determines a crack based on the magnitude of a magnetic field which inevitably varies when a crack occurs, and is thus capable of determining the occurrence of a crack in real time and with precision.

It is noted that the crack determining device discussed above may be one that further comprises a computer to which is constantly transmitted sensing data regarding the magnitude of the magnetic field at the detection part, and it may also further comprise a function whereby, at this computer, if the received sensing data changes, or if the amount of change exceeds a given threshold, it is displayed on screen, or notified by alarm, that a crack has occurred in the solder layer.

In addition, in cases where the magnitude of the magnetic field generated at the generation part, or the change therein, is small, there may be employed a device configuration where, instead of installing an amplifier in the detection part, there is disposed around the generation part a magnetic cover body having an opening on the detection part side, and where the magnitude of the magnetic field generated at the generation part is amplified by this magnetic cover body and detected at the detection part.

Further, in another embodiment of a crack determining device according to the present invention, another detection part distinct from the above-mentioned detection part is disposed near the generation part, and the magnitude of the magnetic field generated at the generation part is detected both at the detection part and the other detection part. It further comprises a map in which, with respect to the magnitude of the magnetic field, which is temperature-dependent, data regarding an actual magnitude of the magnetic field, a temperature associated therewith, and a magnitude of the magnetic field as modified based on this temperature are specified with respect to a plurality of temperatures and a plurality of magnetic fields. The current temperature is determined based on the magnitude of the magnetic field detected at the other detection part by referring to the map. The magnitude of the magnetic field detected at the detection part is taken to be the modified magnitude of the magnetic field based on the determined temperature and the map, and it is determined that a crack has occurred in the solder layer if this modified magnitude of the magnetic field varies from the magnitude of the magnetic field that had been detected before the crack occurred.

Takes into account the fact that the magnitude of a magnetic field is temperature-dependent, a determining device of this embodiment detects the magnitude of the magnetic field generated at the generation part at the other detection part in the vicinity thereof, modifies the magnitude of the magnetic field detected by the detection part disposed within the solder layer based on a temperature derived from the magnitude of the magnetic field detected at the other detection part, and determines the presence/absence of a crack occurrence by comparing whether or not this modified magnitude of the magnetic field varies from a previous magnitude of the magnetic field.

To that end, it is necessary to prepare in advance a map in which data regarding the actual magnitude of a magnetic field, the temperature associated therewith, and the magnitude of the magnetic field as modified based on this temperature are specified with respect to a plurality of temperatures and a plurality of magnetic fields, and it is preferable that pre-specified map data be internally stored within the computer mentioned above, the modified magnitude of the magnetic field be instantly determined upon transmission of the data detected at the two detection parts to the computer, and the presence/absence of a crack occurrence be thus determined.

Further, the present invention also encompasses semiconductor devices comprising a crack determining device mentioned above.

As the presence/absence of a crack occurrence within a solder layer is thus determined in real time and with precision, it becomes possible to prevent semiconductor device failure. In addition, the user of an electronic device in which this semiconductor device is mounted, or a passenger in a hybrid vehicle, electric vehicle, etc., would be able to stop the operation thereof before the semiconductor device becomes inoperable, and it becomes possible to prevent accidents caused by semiconductor devices ceasing to operate.

Effects of the Invention

As can be understood from the descriptions above, according to a crack determining device of the present invention, a generation part that generates a magnetic field is disposed within a constituent member of a semiconductor device, and a detection part that detects the magnitude of a magnetic field and a change therein is disposed within a solder layer in which cracks may occur. Thus, it is possible to determine the occurrence of a crack in the solder layer in real time and with precision.

BRIEF DESCRIPTION OF THE DRAWINGS

FIG. 9($a$) is a diagram in which the closed magnetic circuit in FIG. 7 is illustrated with a virtual magnetic circuit, and FIG. 9($b$) is a view in which the closed magnetic circuit in FIG. 8 is illustrated with a virtual magnetic circuit.

FIG. 10($a$) is a schematic view showing still another embodiment of a crack determining device of the present invention and a semiconductor device comprising same, and FIG. 10($b$) is a chart illustrating the control flow thereof.

LIST OF REFERENCE NUMERALS

1 . . . semiconductor element, 2 . . . circuit board, 3 . . . insulating substrate, 4 . . . heat sink, 5 . . . solder layer, 6 . . . lead frame, 7 . . . magnet (generation part), 7A . . . coil (generation part), 8 . . . MI element (detection part), 9 . . . magnetic cover body, 10, 10A, 10B, 10C, 10D, 10E . . . crack determining device, 20, 20A, 20B, 20C, 20D, 20E . . . semiconductor device, 51 . . . ferromagnetic metal particle, 52 . . . ferromagnetic metal bulk body

BEST MODE FOR CARRYING OUT THE INVENTION

Embodiments of a crack determining device of the present invention and of a semiconductor device comprising same are described below with reference to the drawings. It is noted that the structure of the semiconductor device, that is, the constituent members forming the semiconductor device, the laminate configurations thereof, etc., are, naturally, by no means limited to the illustrated examples. In addition, while there may be further provided a computer to which the detected data at the detection part is transmitted, which modifies the detected data with the current temperature, which displays or warns the occurrence of a crack, etc., illustration thereof is omitted.

Figure 1:
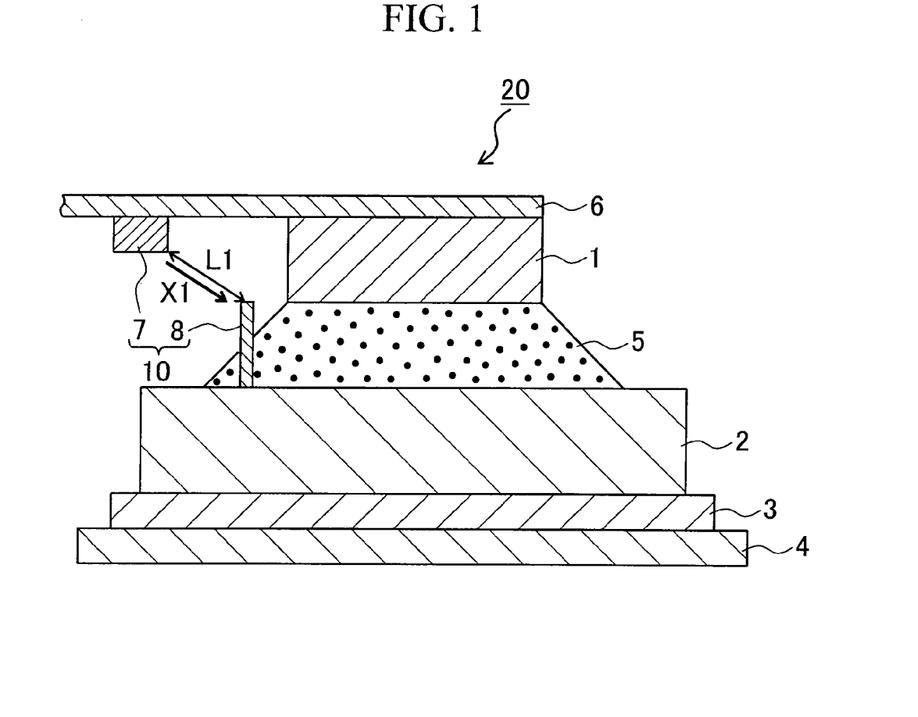
FIG. 1 is a schematic view showing one embodiment of a crack determining device of the present invention and a semiconductor device comprising same.
Figure 2:
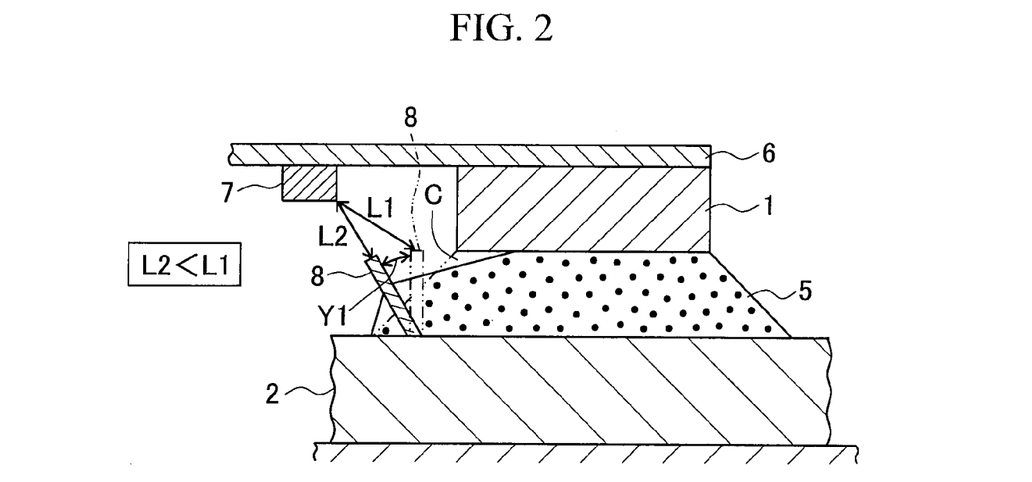
FIG. 2 is a schematic view illustrating a state where a crack has occurred in the solder layer of the semiconductor device in FIG. 1.

FIG. 1 is a view showing one embodiment of a crack determining device of the present invention and a semiconductor device comprising same. FIG. 2 is a view illustrating a state where a crack has occurred in the solder layer of the semiconductor device in FIG. 1.

The semiconductor device 20 shown in the diagram is generally configured by having a solder layer 5 connect a semiconductor element 1 and a circuit board 2, the circuit board 2 and an insulating substrate 3 as well as a heat sink 4 connected by brazing, adhesion, etc., and the semiconductor element 1 connected to a lead frame 6 that communicates with an external electrode.

In addition, in this semiconductor device 20, a magnet 7, which is a generation part that generates a magnetic field, is attached to the lead frame 6, and an MI element 8, which is a detection part that detects the magnitude of the magnetic field generated by the magnet 7 and changes therein, is provided inside the solder layer 5. A crack determining device 10 comprises the magnet 7 and the MI element 8.

While the magnet 7 may be any of a rare-earth magnet, a ferrite magnet, and an alnico magnet, it is preferable that it be formed of a rare-earth magnet, which has a high magnetic flux density, and whose magnitude or changes in magnitude may therefore be detected with better precision with the MI element 8 without having to provide an amplifier, etc.

In the state in FIG. 1, that is, in a state where no crack has occurred in the solder layer 5, the distance between the magnet 7 and the MI element 8 is L1. Magnetic flux flows across this distance from the magnet 7 to the MI element 8 (X1 direction), and the magnitude of the magnetic field (e.g., magnetic flux density) is sensed thereat Through repeated use of the semiconductor device 20, a crack C occurs in the solder layer 5 as shown in FIG. 2. By way of example, as shown in this figure, as the MI element 8 tilts from its original position to an outwardly tilted position (Y1 direction) due to the crack C that has occurred at the upper end part of the solder layer 5, the distance between the magnet 7 and the MI element 8 comes to be distance L2, which is shorter than the original distance of L1.

As the distance shortens, the space resistance between the magnet 7 and the MI element 8 decreases, the magnitude of the magnetic field detected at the MI element 8 changes to a value greater than the value before the crack occurred, and it is determined that the crack C has occurred in the solder layer 5 based on a detection of this change.

Figure 3:
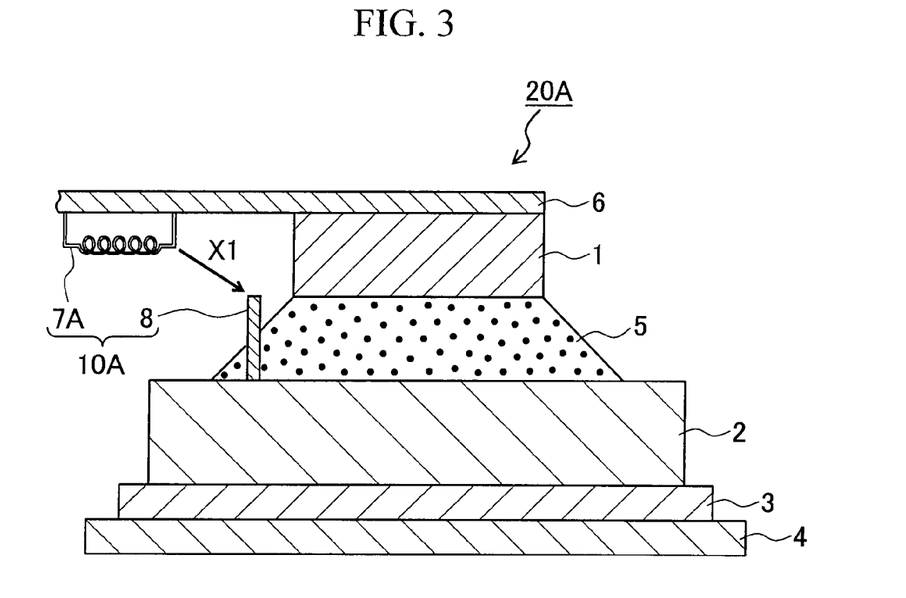
FIG. 3 is a schematic view showing another embodiment of a crack determining device of the present invention and a semiconductor device comprising same.

FIG. 3 is a view showing another embodiment of a crack determining device and a semiconductor device comprising same.

The semiconductor device 20A shown in the diagram is one where, by way of example, a coil 7A in which a conducting wire of a copper material is wound is brazed onto the lead frame 6 of the same material, and where, when a current is passed through the lead frame 6, a magnetic field is generated as a result of a portion of the current flowing through the coil 7A. The magnetic flux generated at the coil 7A flows towards the MI element 8 (X1 direction), and the magnitude of the magnetic field is sensed thereat. A crack determining device 10A comprises the coil 7A and the MI element 8.

Figure 4:
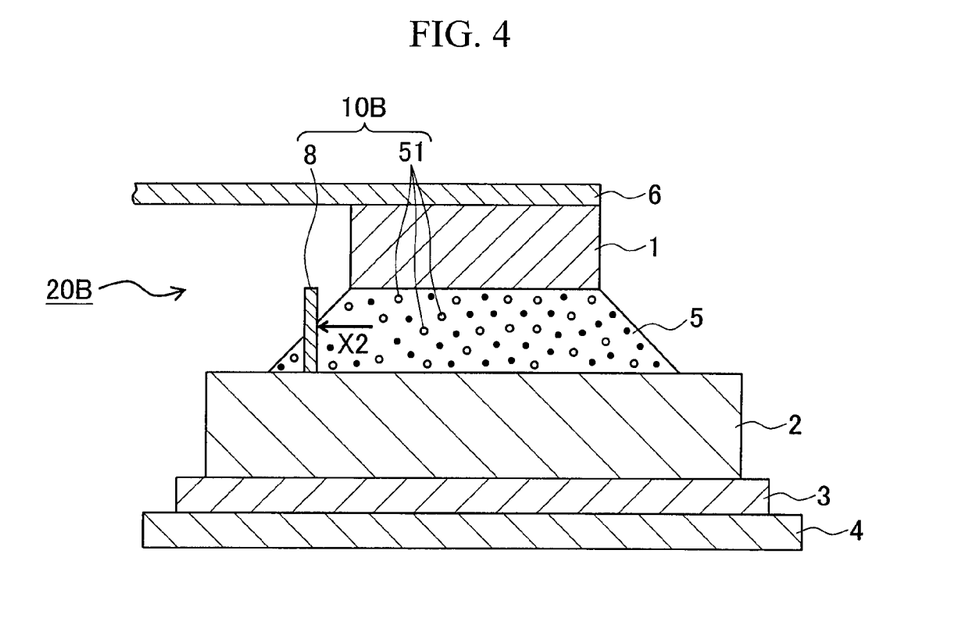
FIG. 4 is a schematic view showing still another embodiment of a crack determining device of the present invention and a semiconductor device comprising same.
Figure 5:
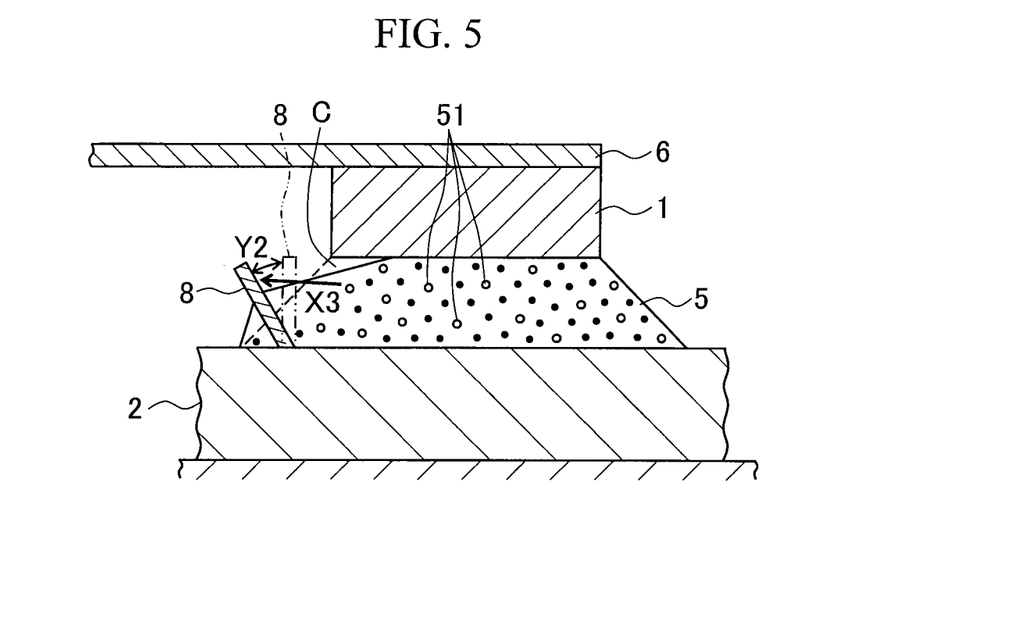
FIG. 5 is a schematic view illustrating a state where a crack has occurred in the solder layer of the semiconductor device in FIG. 4.

In addition, FIG. 4 is a view showing still another embodiment of a crack determining device and a semiconductor device comprising same. FIG. 5 is a view illustrating a state in which a crack has occurred in the solder layer of the semiconductor device in FIG. 4.

In the illustrated semiconductor device 20B, ferromagnetic metal particles 51 are dispersed within the solder layer 5, and these serve as a generation part that generates a magnetic field. A crack determining device 10B comprises the ferromagnetic metal particles 51 and the MI element 8.

In the state in FIG. 4 where no crack has occurred, the magnetic flux from the numerous dispersed metal particles 51 flows towards the MI element 8 (X2 direction), and the sum of the magnitudes of the magnetic fields of the respective metal particles 51 (the magnitude of magnetic field of the metal particles as a collective whole) is detected at the MI element 8.

On the other hand, as a crack C occurs in this solder layer 5 as shown in FIG. 5, and the MI element 8 tilts from its original position to an outwardly tilted position (Y2 direction), the distance between the MI element 8 and the numerous metal particles 51 as a collective whole consequently becomes longer than it originally was. Thus, the distance resistance for the magnetic flux to flow from the metal particles 51 as a collective whole to the MI element 8 (X3 direction) increases, the magnitude of the magnetic field detected at the MI element 8 consequently changes to a value smaller than the value before the crack occurred, and it is determined that the crack C has occurred in the solder layer 5 based on a detection of this change.

Figure 6:
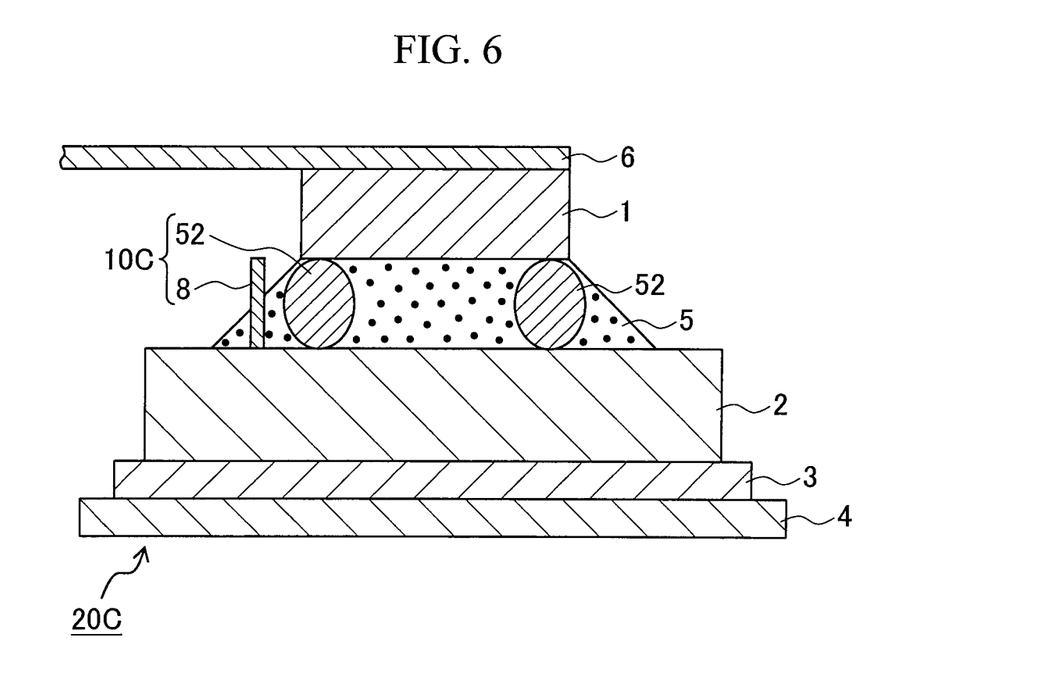
FIG. 6 is a schematic view showing still another embodiment of a crack determining device of the present invention and a semiconductor device comprising same.

In addition, FIG. 6 is a view showing still another embodiment of a crack determining device and a semiconductor device comprising same.

The illustrated semiconductor device 20C is one in which spherical bulk bodies 52, which guarantee a thickness for the solder layer 5, are buried within this solder layer. The bulk bodies 52 are formed of nickel, iron, or cobalt, which are ferromagnetic metals, or of an alloy thereof. Thus, the ferromagnetic metal bulk bodies 52 serve as a generation part that generates a magnetic field, and a crack determining device 10C comprises this and the MI element 8, which is a detection part.

Figure 7:
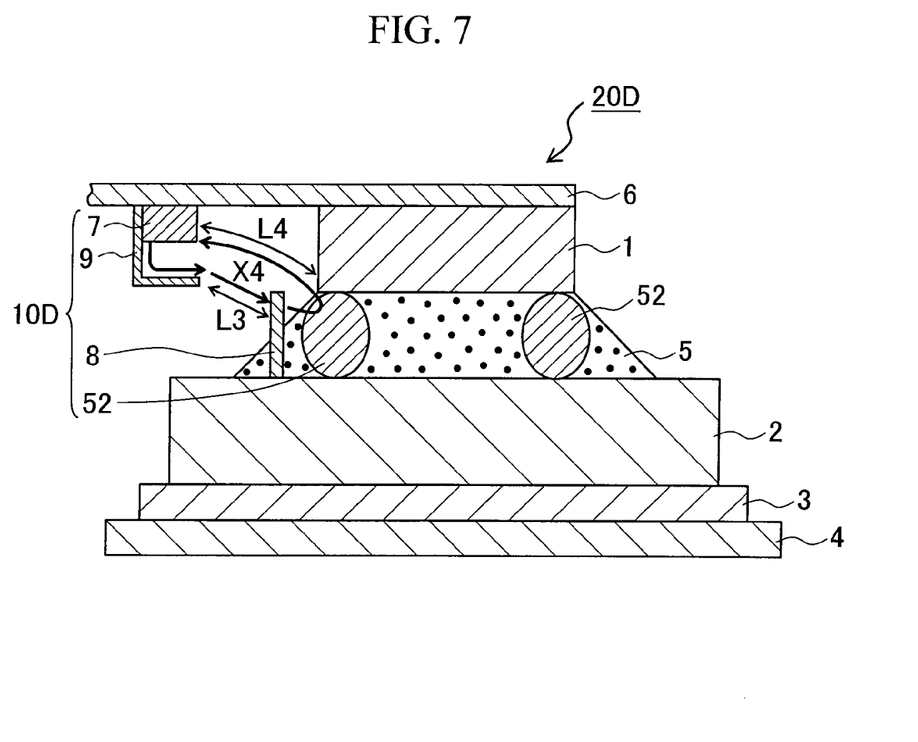
FIG. 7 is a schematic view showing still another embodiment of a crack determining device of the present invention and a semiconductor device comprising same.
Figure 8:
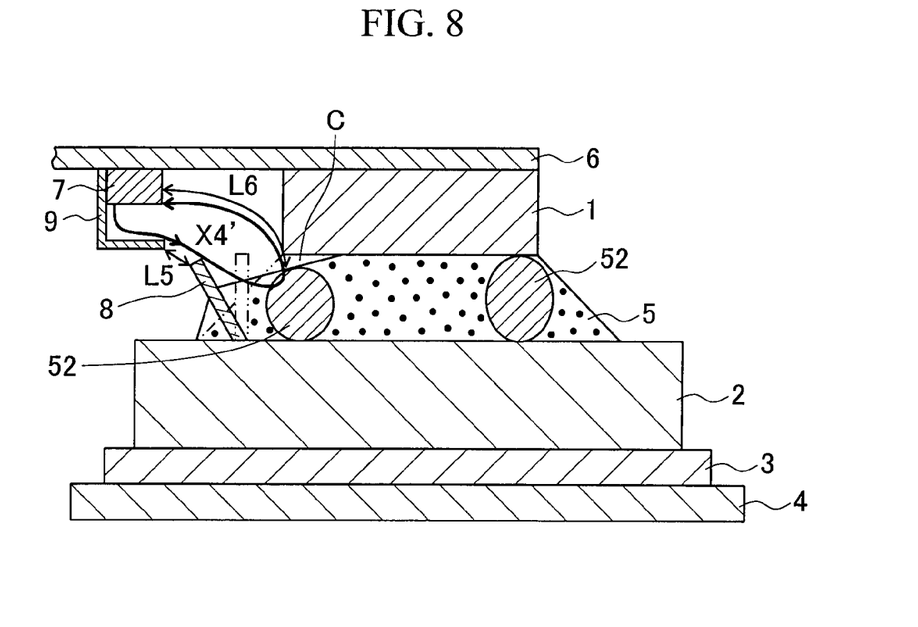
FIG. 8 is a schematic view illustrating a state where a crack has occurred in the solder layer of the semiconductor device in FIG. 7.

In addition, FIG. 7 is a view showing still another embodiment of a crack determining device and a semiconductor device comprising same. FIG. 8 is a view illustrating a state where a crack has occurred in the solder layer of the semiconductor device in FIG. 7.

The illustrated semiconductor device 20D is such that the spherical and ferromagnetic bulk bodies 52, which guarantee a thickness for the solder layer 5, are buried within this solder layer, the magnet 7 is attached to the lead frame 6, and, further, a magnetic cover body 9 having an opening on its MI element 8-side is disposed around this magnet 7, wherein the magnitude of the magnetic field generated at the magnet 7 is amplified by this magnetic cover body 9 and detected at the MI element 8. A crack determining device 10D comprises the magnet 7, the magnetic cover body 9 that supplies the generated magnetic field towards the MI element 8, the ferromagnetic bulk bodies 52, and the MI element 8. It is noted that this crack determining device may also be without any ferromagnetic bulk bodies.

In the state in FIG. 7 where no crack has occurred, the distance between the magnetic cover body 9 and the MI element 8 is L3, and the distance between the ferromagnetic bulk body 52 and the magnet 7 is L4. A magnetic flux flow (X4 direction) of a closed magnetic circuit is formed, where the magnetic flux generated at the magnet 7 passes through the magnetic cover body 9, enters the MI element 8 via a space of distance L3, further passes through the ferromagnetic bulk body 52, and enters the magnet 7 via a space of distance L4.

In contrast, by way of example, when a crack C occurs above the bulk body 52 of the solder layer 5 as shown in FIG. 8, the MI element 8 tilts to the side, and its distance from the magnetic cover body 9 shortens to L5 from the original distance of L3, while, on the other hand, the distance between the bulk body 52 and the magnet 7 lengthens from the original distance of L4 to L6 by an amount corresponding to the crack C (the magnetic flux flow of the closed magnetic circuit is in the X4' direction).

As the two spatial distances L3 and L4 consequently change to L5 and L6, respectively, the space resistance changes, the magnitude of the magnetic field detected at the MI element 8 changes from the value from before the crack occurred, and it is determined that the crack C has occurred in the solder layer 5 based on a detection of this change.

Figure 9:
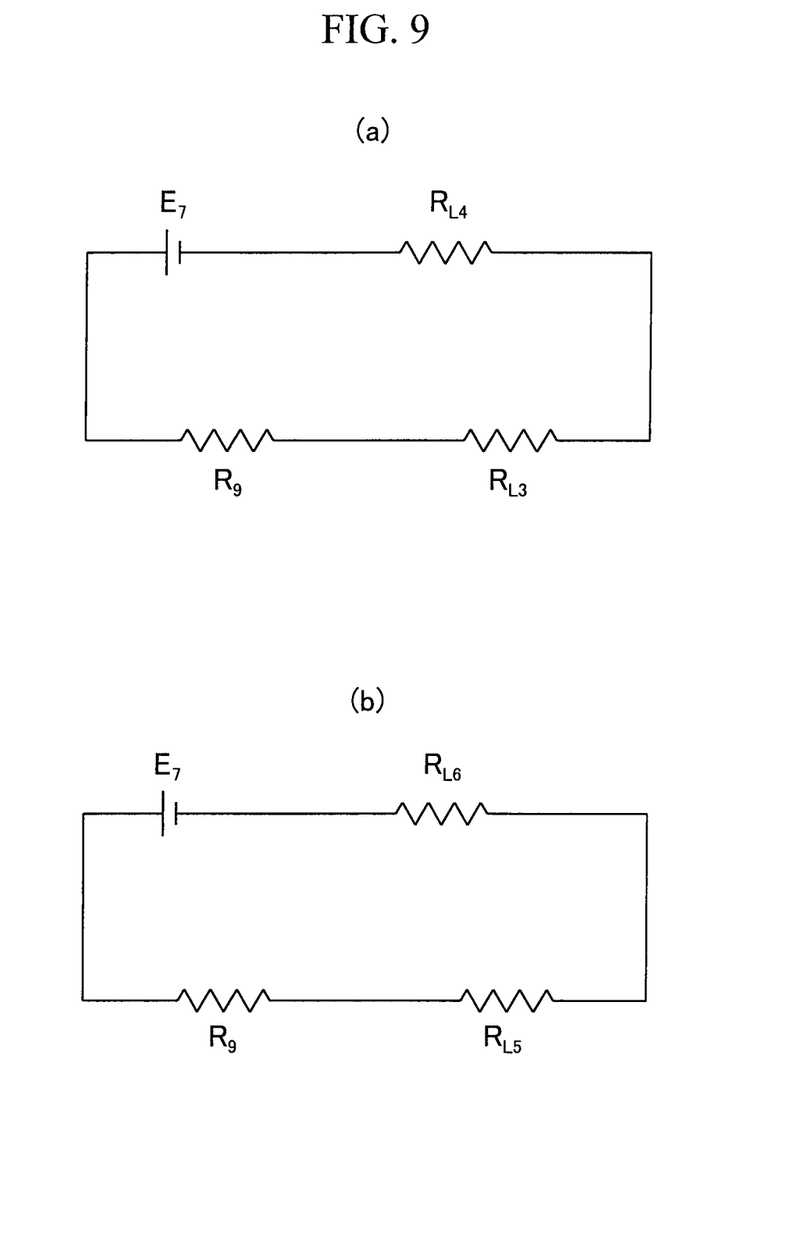

FIGS. 9a and 9b are diagrams that respectively illustrate the above-mentioned closed magnetic circuits relating to FIGS. 7 and 8 with virtual magnetic circuits.

In both FIG. 9a and FIG. 9b, $E_7$ simulates the magnet 7 that generates a magnetic field, $R_9$ simulates the magnetic cover body 9 with a resistance value, and $R_{L3}$, $R_{L4}$, $R_{L5}$ and $R_{L6}$ respectively represent the space resistances of spatial distances L3 through L6.

In addition, FIG. 10a is a view showing still another embodiment of a crack determining device and a semiconductor device comprising same. FIG. 10b is a chart illustrating a control flow thereof.

The illustrated semiconductor device 20E is such that the spherical and ferromagnetic bulk bodies 52, which guarantee a thickness for the solder layer 5, are buried within this solder layer, the magnet 7 is attached to the lead frame 6, and, further, the magnetic cover body 9 having an opening on its MI element 8-side is disposed around this magnet 7, and another MI element 8A is further disposed between this magnet 7 and the magnetic cover body 9 so as to be in contact with the magnet 7. A crack determining device 10E comprises the magnet 7, the magnetic cover body 9, the ferromagnetic bulk bodies 52, the MI element 8, and the other MI element 8A.

Taking into account the fact that the magnitude of a magnetic field is dependent on temperature, the illustrated crack determining device 10E detects the magnitude of the magnetic field generated at the magnet 7 with the other MI element 8A in the vicinity thereof, modifies the magnitude of the magnetic field detected by the MI element 8 disposed within the solder layer 5 based on a temperature derived from the magnitude of the magnetic field detected at the other MI element 8A, and determines the presence/absence of a crack occurrence by comparing whether or not the magnitude of the magnetic field as modified varies from a previous (a state where no crack has occurred) magnitude of the magnetic field.

Figure 11:
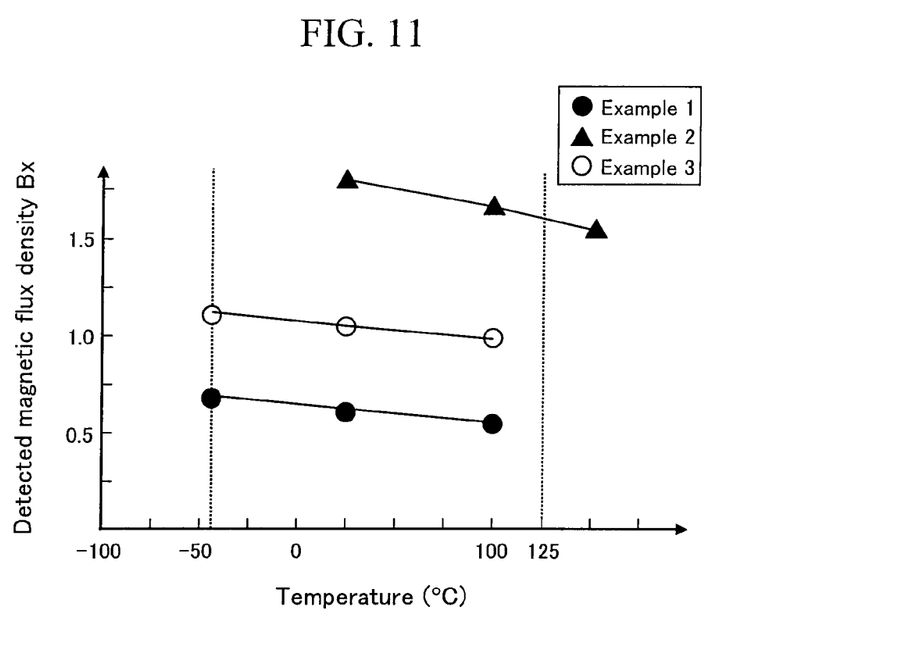
FIG. 11 is a chart illustrating the relationship between detected magnetic flux density and temperature.

FIG. 11 shows the relationship between detected magnetic flux density and temperature, that is, the temperature dependence of the detected magnetic flux density, through a graph based on verification by the present inventors.

Figure 10:
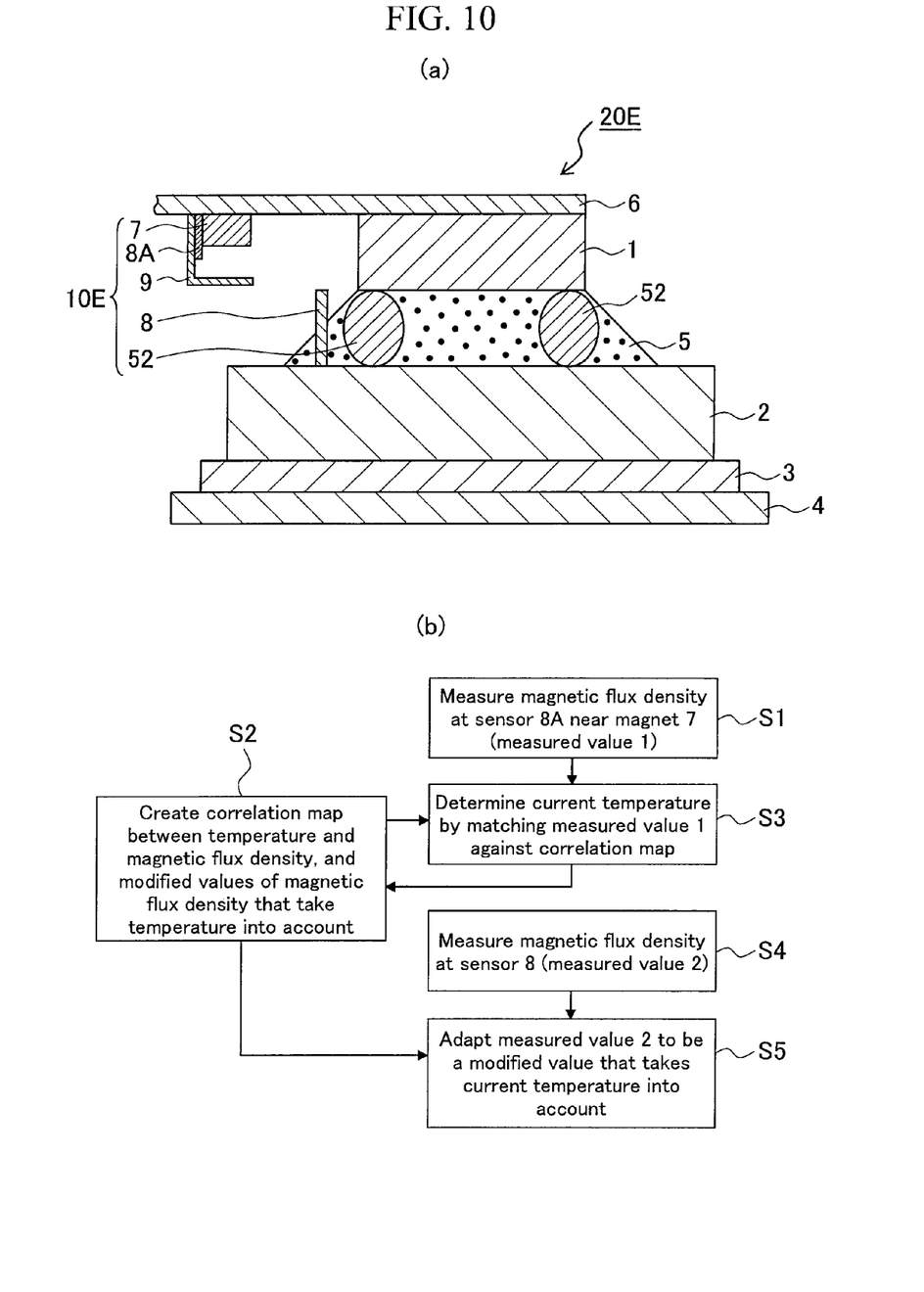

In this figure, Example 1 is of the configuration of the crack determining device 10 shown in FIG. 1, where the magnet 7 comprises a ferrite. Example 2 is similarly of the configuration of the crack determining device 10, where the magnet 7 comprises a rare-earth magnet. Example 3 is of the configuration of the crack determining device 10E shown in FIG. 10, where the magnet 7 comprises a ferrite. In addition, the magnetic flux density detected at the MI element 8A of Example 3 at 100° C. is normalized to 1, and the other magnetic flux density values are indicated in proportion thereto.

As shown in this figure, assuming that the in-use temperature range for the semiconductor device is approximately −40° C. to 130° C. as shown in the figure, it has been determined that there is a tendency for the detected magnetic flux density to decrease linearly as the temperature rises.

Thus, by appropriately modifying the detected magnitude of the magnetic field by taking its temperature dependence into account, it becomes possible to determine with precision whether or not a crack has actually occurred in the solder layer.

Thus, by way of example, based on the control flow shown in FIG. 10b, the magnitude of the magnetic field (magnetic flux density) detected at the MI element 8 is modified based on the temperature determined from the magnitude of the magnetic field detected at the MI element 8A near the magnet 7.

Specifically, the magnetic flux density (measured value 1) is measured at the MI element 8A near the magnet 7 (step S1). On the other hand, a correlation map between temperature and magnetic flux density, and modified values of magnetic flux density that take temperature into account are created in advance based on a verification of FIG. 11, etc. (step S2).

Measured value 1 is matched against the correlation map to determine the current temperature (step S3). On the other hand, magnetic flux density (measured value 2) is measured at the MI element 8 disposed within the solder layer (step S4). By having measured value 2 be a modified value that takes the current temperature into account (step S5), it is possible to determine with precision the magnitude of the magnetic field at the MI element position in the solder layer.

This modified magnitude of the magnetic field is then compared with the previous magnitude of the magnetic field, and it is determined that a crack has occurred if there is any change.

Figure 12:
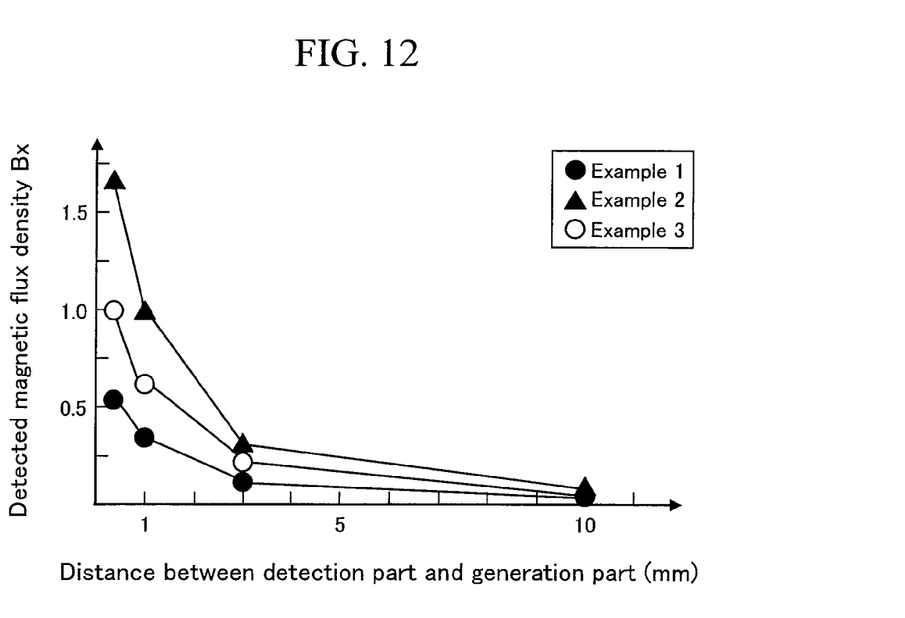
FIG. 12 is a chart illustrating the relationship between detected magnetic flux density and the distance between the detection part and the generation part.

In addition, FIG. 12 is a chart in which the relationship between detected magnetic flux density and distance between the detection part and the generation part has been determined through verification by the present inventors. It is noted that, in this figure, Examples 1 to 3 are similar to those in FIG. 11.

In this figure, it can be seen that as the distance between the detection part and the generation part draws nearer, the detection sensitivity for magnetic flux density increases markedly.

However, once this distance becomes shorter than 1 mm, while detection sensitivity may be extremely high, the magnetic field generated at the generation part could potentially affect the performance of the semiconductor element. Thus, it is preferable that the illustrated crack determining devices be configured with 1 mm being defined as the shortest distance between the detection part and the generation part.

Thus, according to the illustrated crack determining devices of the present invention and the semiconductor devices comprising same, it is possible to determine, in real time and with precision, the fact that a crack has occurred in the solder layer.

While embodiments of the present invention have thus been described in detail using the drawings, specific configurations are by no means limited to such embodiments, and design modifications, etc., made within a scope that does not depart from the spirit of the present invention are included in the present invention.

The invention claimed is:

1. A crack determining device that determines whether or not a crack has occurred in a solder layer with respect to a semiconductor device in which at least a semiconductor element is connected to a connectee member via the solder layer, the crack determining device comprising:
    a generation part that generates a magnetic field and that is fixed to a member forming the semiconductor device; and
    a detection part that detects a magnitude of a magnetic field and that is disposed within the solder layer, wherein
    the magnetic field generated at the generation part is detected at the detection part, and it is determined that a crack has occurred in the solder layer if this magnitude of the magnetic field varies from a magnitude of the magnetic field detected before the crack occurred.

2. The crack determining device according to claim 1, wherein the generation part comprises a magnet.

3. The crack determining device according to claim 1, wherein the semiconductor device comprises a lead frame that extends to the outside from the semiconductor element, and wherein a coil is attached to the lead frame and is adapted to be the generation part, and a portion of an electric current flowing through the lead frame is passed through the coil to generate a magnetic field.

4. The crack determining device according to claim 1, wherein a magnetic cover body having an opening on the detection part-side is disposed around the generation part, and wherein the magnitude of the magnetic field generated at the generation part is amplified by this magnetic cover body and detected at the detection part.

5. The crack determining device according to claim 1,
wherein another detection part distinct from the detection part is disposed near the generation part,
wherein the magnitude of the magnetic field generated at the generation part is detected at both the detection part and the other detection part,
wherein the crack determining device further comprises a map in which, with respect to the magnitude of the magnetic field, which is temperature-dependent, data regarding an actual magnitude of the magnetic field, a temperature associated therewith, and a magnitude of the magnetic field as modified based on this temperature are specified with respect to a plurality of temperatures and a plurality of magnetic fields, and
wherein a current temperature is determined from the magnitude of the magnetic field detected at the other detection part by referring to the map, the magnitude of the magnetic field detected at the detection part is adapted to be the modified magnitude of the magnetic field based on the determined temperature and the map, and it is determined that a crack has occurred in the solder layer if this modified magnitude of the magnetic field varies from the magnitude of the magnetic field detected before the crack occurred.

6. A semiconductor device comprising the crack determining device according to claim 1.

7. A crack determining device that determines whether or not a crack has occurred in a solder layer with respect to a semiconductor device in which at least a semiconductor element is connected to a connectee member via the solder layer, the crack determining device comprising:
a generation part comprising a ferromagnetic metal and that generates a magnetic field within the solder layer; and
a detection part that detects a magnitude of a magnetic field and that is disposed within the solder layer, wherein
the magnetic field generated at the generation part is detected at the detection part, and it is determined that a crack has occurred in the solder layer if this magnitude of the magnetic field varies from a magnitude of the magnetic field detected before the crack occurred.

8. The crack determining device according to claim 7, wherein the ferromagnetic metal is dispersed within the solder layer.

9. The crack determining device according to claim 7, wherein the ferromagnetic metal is a bulk body that is buried within the solder layer and that maintains the thickness of the solder layer.

10. The crack determining device according to claim 7, wherein the ferromagnetic metal comprises one of nickel, iron, cobalt, and an alloy thereof.

11. The crack determining device according to claim 7, wherein a magnetic cover body having an opening on the detection part-side is disposed around the generation part, and wherein the magnitude of the magnetic field generated at the generation part is amplified by this magnetic cover body and detected at the detection part.

12. The crack determining device according to claim 7,
wherein another detection part distinct from the detection part is disposed near the generation part,
wherein the magnitude of the magnetic field generated at the generation part is detected at both the detection part and the other detection part,
wherein the crack determining device further comprises a map in which, with respect to the magnitude of the magnetic field, which is temperature-dependent, data regarding an actual magnitude of the magnetic field, a temperature associated therewith, and a magnitude of the magnetic field as modified based on this temperature are specified with respect to a plurality of temperatures and a plurality of magnetic fields, and
wherein a current temperature is determined from the magnitude of the magnetic field detected at the other detection part by referring to the map, the magnitude of the magnetic field detected at the detection part is adapted to be the modified magnitude of the magnetic field based on the determined temperature and the map, and it is determined that a crack has occurred in the solder layer if this modified magnitude of the magnetic field varies from the magnitude of the magnetic field detected before the crack occurred.

13. A semiconductor device comprising the crack determining device according to claim 7.

* * * * *